(12) United States Patent
Charlton et al.

(10) Patent No.: US 6,486,106 B1
(45) Date of Patent: Nov. 26, 2002

(54) COMPOSITION

(75) Inventors: Lynda Rosemary Charlton, Staines (GB); Juliet Teresa McGillycuddy, Bracknell (GB); Sharon Owen, Feltham (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/693,055

(22) Filed: Oct. 20, 2000

Related U.S. Application Data

(63) Continuation-in-part of application No. 09/194,383, filed on Nov. 25, 1998, now Pat. No. 6,162,774.

(30) Foreign Application Priority Data

Jun. 10, 1996 (GB) ............................................. 9612067

(51) Int. Cl.$^7$ .............................. A61K 7/50; C11D 7/22
(52) U.S. Cl. ...................... 510/130; 510/159; 510/405; 510/470; 510/477; 510/488; 510/505
(58) Field of Search ................................. 510/130, 159, 510/405, 470, 477, 488, 505

(56) References Cited

U.S. PATENT DOCUMENTS

| | | | |
|---|---|---|---|
| 4,971,800 A | | 11/1990 | Chess et al. ................. 424/449 |
| 5,011,681 A | * | 4/1991 | Ciotti et al. ................... 424/81 |
| 5,045,317 A | | 9/1991 | Chess et al. ................. 424/401 |
| 5,051,260 A | | 9/1991 | Chess et al. ................. 424/449 |
| 5,431,840 A | * | 7/1995 | Soldanski et al. ..... 252/174.17 |
| 5,653,970 A | * | 8/1997 | Vermeer ................... 424/70.24 |
| 5,989,536 A | * | 11/1999 | Deckner et al. ......... 424/78.05 |

FOREIGN PATENT DOCUMENTS

| | | |
|---|---|---|
| WO | WO/9503781 | 2/1995 |

OTHER PUBLICATIONS

"Polyolprepolymers: Properties and Uses in Cosmetic Products" Penederm Inc., 1994.

* cited by examiner

Primary Examiner—Bruce H. Hess
Assistant Examiner—Dawn Garrett
(74) Attorney, Agent, or Firm—Nora Stein-Fernandez

(57) ABSTRACT

A skin wash composition intended for topical application to water-wetted skin comprising an α-hydroxy acid active ingredient formulated in a mild and non-irritant detergent base consisting of a mixture of a non-ionic alkypolyglucoside surfactant and an amphoteric surfactant.

6 Claims, No Drawings

COMPOSITION

This is a continuation-in-part of application Ser. No. 09/194,383 filed Nov. 25, 1998, now U.S. Pat. No. 6,162,774.

The present invention relates to compositions for topical application to the skin surface, in particular to skin wash compositions which are applied to water-wetted skin and subsequently rinsed off with water. Specifically, the present invention relates to skin wash compositions comprising an α-hydroxy acid as an active ingredient formulated in a mild and non-irritant detergent base.

The class of compounds generally known in the field of cosmetic and therapeutic skin treatments as α-hydroxy acids includes compounds such as salicylic acid, lactic acid and glycolic acid. These compounds constitute the active ingredients of a number of commercially available products which are applied to the skin in order to confer a beneficial effect with respect to appearance and skin condition, in particular smoothness and suppleness. Salicylic acid for example has been shown to have keratolytic and comedolytic activity as well as anti-bacterial efficacy and has been used in the treatment and prevention of mild to moderate acne for more than 100 years. Lactic acid has a beneficial effect on skin hydration and is a constituent of a number of skin tonic and moisturising products.

α-Hydroxy acids, whilst conferring a beneficial effect on the skin, may cause local irritation when applied to sensitive areas of the skin, in particular the face. Moreover, local irritation may be exacerbated by the carrier system in which the active ingredient is formulated. For example, skin wash compositions and in particular face wash compositions which are generally formulated with a soap-free detergent base selected for effective cleansing and foaming, may confer an irritant effect due to the use of ionic surfactants commonly employed in such detergent systems.

A further problem associated with formulating compositions containing α-hydroxy acids arises because of the desirability to formulate the composition at an acid pH at which the most efficacious free-acid form of the α-hydroxy acid will predominate. For skin wash compositions, this problem is exacerbated by the difficulty of obtaining a detergent base system at sufficiently low pH. A skin wash composition described as having a gentle yet effective cleanser for acne treatment and containing 2.0% w/w salicylic acid in a detergent base comprising a mixture of anionic and amphoteric surfactants is commercially available. Analysis of this product shows that it has a pH of 5. It follows, having regard to the pKa of salicylic acid which is attributed the value 2.97, that the free-acid form of the α-hydroxy acid does not predominate in this product and that its efficacy is accordingly not fully optimised.

It is an object of the present invention to provide a skin wash composition containing an α-hydroxy acid and a detergent base which has good cleansing and foaming characteristics, is mild and non-irritant and wherein the pH of the composition approaches the pKa of the α-hydroxy acid such that the efficacy of the α-hydroxy acid is enhanced. This object is achieved according to the present invention which is based on the unexpected finding that a detergent base comprising a mixture of a non-ionic alkylpolyglucoside surfactant and an amphoteric surfactant not only has the desired cleansing and foaming characteristics and is mild and non-irritant when applied to the skin but also enables compositions to be formulated at low pH.

According to the present invention there is provided a skin wash composition comprising from 0.1 to 10% w/w of an α-hydroxy acid and a detergent base consisting of a mixture of a non-ionic alkylpolyglucoside surfactant and an amphoteric surfactant wherein the pH of the composition is in the range 3.0 to 4.5.

Suitable α-hydroxy acids for incorporation into skin wash compositions of the invention include salicylic acid, lactic acid, citric acid, glycolic acid, malic acid, maleic acid, pyruvic acid and hydroxy-octanoic acid. Preferred α-hydroxy acids are salicylic acid, lactic acid and glycolic acid, especially salicylic acid and lactic acid. Salicylic acid will suitably be present in compositions of the invention at a concentration in the range 0.2 to 5.0% w/w, more suitably in the range 1.0 to 3.0% w/w. A preferred concentration for salicylic acid is 2.0% w/w. Lactic acid will suitably be present in compositions of the invention at a concentration in the range 0.1 to 5.0% w/w, more suitably in the range 0.5 to 2.5% w/w. A preferred concentration for lactic acid is 1% w/w. Glycolic acid will suitably be present at a concentration in the range 2.0 to 10.0% w/w.

As used herein, the term alkylpolyglucoside surfactant means a non-ionic surfactant derived from common natural organic monomer units as found in starch, fats and sugars, and most suitably derived from D-glucose monomer units. Alkylpolyglucosides derived from D-glucose are acetal compounds in which the alkyl residue has a carbon chain length of from 8 to 16 carbon atoms and the degree of glucosidation (or polymerisation), i.e., the average number of glucose units per alkyl radical, is between 1.1 and 6. A range of suitable alkylpolyglucosides are commercially available either individually or as mixtures or blends. Compositions according to this invention will generally contain mixtures or blends of different alkylpolyglucosides. Preferred alkylpolyglucosides for use in the present invention include decyl glucoside and lauryl glucoside and mixtures thereof. Alkylpolyglucoside surfactants generally comprise up to 20% w/w of the skin wash composition, suitably from 2.0 to 15.0% w/w and preferably from 4.0 to 10.0% w/w of the composition. It will be appreciated that the amount of alkylpolyglucoside will be determined to some extent by the nature and amount of amphoteric surfactant present in the composition.

In principle, any amphoteric surfactant which is acceptable for topical application to the skin may contribute, with the alkylpolyglucoside surfactant, to the detergent base but, in view of their inherent mildness and good foaming performance, the preferred amphoteric surfactant will belong to the class of compounds known as betaines. Structurally, betaine compounds contain a carboxylate functional group and a quaternary nitrogen function separated by a methylene moiety. They include n-alkyl betaines such as cetyl betaine and behenyl betaine, and n-alkylamido betaines such as cocoamidopropyl betaine. The amphoteric surfactant component of the detergent base for compositions of the present invention may be a single compound or a mixture of blend of two or more different substances. A preferred amphoteric surfactant is cocoamidopropyl betaine. Amphoteric surfactants will generally comprise up to 10% w/w of the skin wash composition, suitably from 2.0 to 8.0% w/w and preferably from 2.5 to 6.0% w/w of the skin wash composition. The amount of amphoteric surfactant will to some extent be determined by the alkylpolyglucoside surfactant component of the detergent base.

Typically, the detergent base consisting of the mixture of non-ionic alkylpolyglucoside surfactant and amphoteric surfactant will constitute up to 30% w/w of the skin wash composition. Suitably the detergent base will constitute from 5.0 to 20.0% w/w and more suitably from 8.0 to 18.0% w/w of the skin wash composition.

Control of pH to within defined limits is an essential feature of the present invention. A pH within the desired range 3.0 to 4.5 is conferred partly by the inherent properties of the α-hydroxy acid and specific surfactants and quantities thereof making up the detergent base and partly, where required, by use of a suitable neutralising agent for the α-hydroxy acid. Any topically acceptable neutralising agent which is compatible with the other components of the composition can be used. It has been found that the neutralising agent tromethamine is particularly suitable for skin wash compositions containing α-hydroxy acids. Other suitable neutralising agents include sodium hydroxide and triethanolamine. The amount of neutralising agent will be determined by the acid/base properties of the other ingredients which make up the composition and the pH selected for the composition.

The skin wash compositions of the invention may also contain additional topically acceptable skin conditioning and soothing agents, for example in the form of anti-inflammatory agents and vitamins or vitamin derivatives, typically at low concentrations, for example in the range 0.01 to 2.0% w/w of the total composition. Examples of topically acceptable anti-inflammatory agents include allantoin and bisabolol. A preferred vitamin derivative is vitamin E acetate which has anti-inflammatory properties.

The skin wash compositions of the present invention may also contain topically acceptable polymers for increasing deposition of the active ingredient on and in the upper layers of the skin. Advantageously such polymers serve to prolong activity of an active ingredient(s) by enhancing skin substantivity, i.e., resistance to wash off. The deposition aiding polymers that are useful herein are urethane polymers including the hydroxy-terminated urethane polymers that are generally described in U.S. Pat. Nos. 4,971,800; 5,051,260 and 5,045,317 all issued to Chess et al. These polymers are represented by the general formula

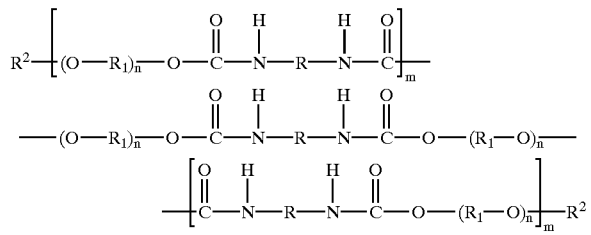

wherein:
R and $R_1$ are independently selected from an optionally substituted alkylene or alkenylene radical having from 1 to 20 carbon atoms, or a cycloalkylene or cycloalkenylene radical containing from 5 to 10 carbon atoms, or a mononuclear or fused ring arylene radical containing from 6 to 10 carbon atoms;
within the definition of alkylene is cycloalkylene, e.g., dicyclohexyl methylene;
preferably $R_1$ is an alkylene radical such as propylene radical linked in the 1,2 position;
$R^2$ is hydrogen or a methyl or ethyl group; preferably $R^2$ is hydrogen; m is a number in the range 0 to 6, preferably 1 to 4; and n is an integer preferably in the range 8 to 51.

Preferred hydroxy-terminated polymers useful herein are those designated by the following CAS names:
Poly[oxy(methyl-1,2-ethanediyl)],α-hydro-ω-hydroxy polymer with 1,1'methylene-bis-[4,isocyanatocyclohexane] and Poly (oxy(1,2-ethanediyl),α-hydro-ω-hydroxy polymer with 1,1' methylene-bis-[4,isocyanatocyclohexane].

Especially preferred polymers are those known by their CTFA designations as Polyolprepolymer-2, Polyolprepolymer-14 and Polyolprepolymer-15, and in particular water-insoluble polyolprepolymers such as the aforementioned Polyolprepolymer-2 and Polyolprepolymer-14. These polyolprepolymers are commercially available as Topicare Delivery Compounds® from Penederm Inc, 320 Lakeside Dr., Ste.A, Foster City, Calif. 944404-1146.

The urethane polymers described herein may generally comprise up to 10% w/w of the skin wash composition, suitably from 1 to 8% w/w, and preferably 2 to 5% w/w of the skin wash composition. Suitably compositions comprising the urethane polymer(s) may further comprise a stabilizing agent, suitably in an amount ranging from 0.01 to 2% w/w, preferably from 0.1 to 0.5% w/w. In principle any stabilizing agent may be used which is acceptable for topical application to the skin and suitable for use within the pH range of the invention e.g. an acrylic acid/vinyl ester copolymer, available as Stabylen 30, from 3V Sigma S.P.A., Third Floor, Clarendon House, Stamford New Road, Altrincham, Cheshire WA14 1BY.

Additionally, compositions of the present invention will suitably contain pharmaceutically and cosmetically acceptable additives or excipients conventional in the field of topical medicines and cosmetics, including for example thickeners, moisturisers, re-fatting agents, preservatives, conditioners, chelating agents, colouring agents, fragrances, UV filters and/or emulsifiers. The additives or excipients used in any given composition will be compatible both with each other and with the essential ingredients of the composition such that there is no interaction which would impair the performance of the active ingredients. All additives or excipients must of course be non-toxic and of sufficient purity to render them suitable for human use.

Suitable thickeners include polymeric high molecular weight, non-ionic surfactants consisting of a long chain ($C_{12}$ to $C_{18}$) polyethylene glycol fatty acid or fatty acid residue. Examples include PEG 200 hydrogenated glyceryl palmitate, PEG 55 propylene glycol oleate, PEG 150 distearate and PEG 200 glyceryl tallowate. Suitable low molecular weight thickeners include cocamide DEA, laureth-3 and glyceryl monolaurate. A thickener comprising a polyurethane resin, propylene glycol and water sold under the trade name Acrysol 44 also performs well in detergent base skin wash compositions. A thickener will suitably comprise up to 10.0% w/w of the composition, more suitably from 2.0 to 5.0% w/w. Preferred moisturisers include glycerin, propylene glycol, sorbitol and polyethylene glycol. A moisturiser may comprise up to 15% w/w of the composition, more generally from 2.0 to 6.0% w/w of the composition. Suitable re-fatting agents generally comprising 0.5 to 5.0% w/w of the composition, preferably 0.75 to 2.0% w/w include polyethylene glycol 7 and glyceryl cocoate. Suitable preservatives generally comprising 0.01 to 1.00% w/w of the composition and suitably 0.10 to 0.30% w/w, include phenoxyethanol and methyl dibromo glutaronitrile and mixtures thereof. Suitable conditioners, generally comprising 0.1 to 5.0% w/w of the composition and suitably 1.0 to 3.5% w/w include hydroxycetyl hydroxyethyl dimonium chloride and polyquaternium 39. Suitable chelating agents, generally comprising up to 1.0% w/w of the composition and suitably 0.1 to 0.3% w/w include ethylene diamine tetra-acetic acid (EDTA), hydroethylene diamine triacetic acid (HEEDTA), diethylene triamine penta-acetic acid (DPTA) and cyclohexane diamine tetra-acetic acid (CTDA).

The balance of the composition is typically water and/or other non-alcohol solvent so as to make up 100% w/w of the composition. The preferred solvent is water which will generally constitute more than 50% w/w of the skin wash composition. Other suitable non-alcohol solvents which may be included to aid solution of the α-hydroxy acid include glycols such as propylene glycol and macrogols.

The skin wash compositions of the invention may be prepared by methods well known in the art and readily available to the skilled formulator. Generally the α-hydroxy acid and the surfactants making up the detergent base, together with any additives, are dissolved in solvent, the pH of the resulting mixture is checked and adjusted if appropriate and the viscosity of the composition is set to the desired level by addition of thickening agents. The present invention extends to a process for preparing a skin was composition as hereinbefore defined comprising the admixture of the α-hydroxy acid with the detergent base in an aqueous solvent system and adjusting the pH as required such that the pH of the composition is in the range 3.0 to 4.5.

The present invention additionally encompasses the use of a skin wash composition as hereinbefore defined wherein the α-hydroxy acid is salicylic acid for the manufacture of a medicament for the treatment and/or prophylaxis of acne. The use of compositions of the present invention as hereinbefore defined as a cosmetic treatment for improving the appearance and condition of human skin also forms part of the invention.

The following examples further describe and demonstrate compositions falling within the scope of the invention. For the avoidance of doubt, the examples are solely for the purpose of illustration and are not limiting with respect to the scope of the invention.

EXAMPLE 1

Skin Wash Composition Containing Lactic Acid

A composition comprising the following ingredients was prepared. The resulting composition had a pH of approximately 3.5.

| Ingredient | | % w/w |
|---|---|---|
| α-hydroxy acid: | lactic acid | 1.0 |
| detergent base: | decyl glucoside | 3.5 |
| | lauryl glucoside | 3.6 |
| | cocoamidopropyl betaine | 5.0 |
| thickener: | PEG 120 methyl glucose dioleate | 3.2 |
| preservative: | phenoxyethanol | 0.25 |
| solvent: | water | to 100% |

EXAMPLE 2

Skin ash Composition Containing Salicylic Acid

A composition comprising the following ingredients was prepared. The resulting composition was a clear product having a pH of 4.5.

| Ingredient | | % w/w |
|---|---|---|
| α-hydroxy acid: | salicylic acid | 2.0 |
| detergent base: | lauryl glucoside | 2.4 |
| | decyl glucoside | 2.0 |
| | cocamidopropyl betaine | 2.8 |
| neutralising agent: | Tromethamine | 1.5 |
| thickener: | PEG 120 methyl glucose dioleate | 4.0 |
| solvent: | de-ionised water | to 100% |

EXAMPLE 3

Skin Wash Composition Containing Salicylic Acid

The composition of Example 2 containing the additional excipients indicated below was prepared. The resulting clear product had a pH of 4.5.

conditioner: hydroxycetyl hydroxyethyl dimonium chloride chelating agent: EDTA preservative: phenoxyethanol anti-inflammatory agent: allantoin & vitamin E acetate

| Component | % w/w | % w/w | % w/w |
|---|---|---|---|
| EXAMPLE 4 - Skin Wash Compositions | | | |
| Salicylic Acid | 2.00 | 2.00 | — |
| Lactic Acid | — | — | 1.00 |
| Decyl glucoside | 3.50 | 3.50 | 3.50 |
| Lauryl polyglucoside | 3.60 | 3.60 | 3.60 |
| Cocamidopropyl betaine | 5.00 | 5.00 | 5.00 |
| PEG 120 methyl glucose dioleate | 10.00 | 10.00 | 10.00 |
| Phenoxyethanol | 0.25 | 0.25 | 0.25 |
| Sodium hydroxide | 0.15 | — | — |
| Tromethamine | — | 1.50 | — |
| Polyolprepolymer 2 | 3.00 | 3.00 | 3.00 |
| Water to | 100% | 100% | 100% |
| The lactic acid composition forms a hazy gel having a pH 3.65 and a viscosity of 8,500 cP at 25° C. | | | |
| EXAMPLE 5 - Skin Wash Composition | | | |
| Salicylic Acid | 2.00 | 2.00 | — |
| Lactic Acid | — | — | 1.00 |
| Decyl glucoside | 2.00 | 2.00 | 2.00 |
| Lauryl polyglucoside | 2.40 | 2.40 | 2.40 |
| Cocamidopropyl betaine | 2.80 | 2.80 | 2.80 |
| PEG 120 methyl glucose dioleate | 10.00 | 10.00 | 10.00 |
| Phenoxyethanol | 0.25 | 0.25 | 0.25 |
| Sodium hydroxide | 0.15 | — | — |
| Tromethamine | — | 1.50 | — |
| Polyolprepolymer 2 | 3.00 | 3.00 | 3.00 |
| Water to | 100% | 100% | 100% |
| The lactic acid composition forms a hazy gel having a pH 3.32 and a viscosity of 8,000 cP at 25° C. | | | |
| EXAMPLE 6 - Skin Wash Composition | | | |
| Salicylic Acid | 2.00 | 2.00 | — |
| Lactic Acid | — | — | 1.00 |
| Decyl glucoside | 2.00 | 2.00 | 2.00 |
| Lauryl polyglucoside | 2.40 | 2.40 | 2.40 |
| Cocamidopropyl betaine | 2.80 | 2.80 | 2.80 |
| PEG 120 methyl glucose dioleate | 10.00 | 10.00 | 10.00 |
| Phenoxyethanol | 0.25 | 0.25 | 0.25 |
| Stabylen 30 | 0.10 | 0.10 | 0.10 |
| Sodium hydroxide | 0.15 | — | — |
| Tromethamine | — | 1.50 | — |
| Polyolprepolymer 2 | 3.00 | 3.00 | 3.00 |
| Water to | 100% | 100% | 100% |
| The lactic acid composition forms a clear gel having a pH 3.38 and a viscosity of 14,500 cP at 25° C. | | | |
| EXAMPLE 7 - Skin Wash Composition | | | |
| Salicylic Acid | 2.00 | 2.00 | — |

| Component | % w/w | % w/w | % w/w |
|---|---|---|---|
| Lactic Acid | — | — | 1.00 |
| Decyl glucoside | 3.50 | 3.50 | 3.50 |
| Lauryl polyglucoside | 3.60 | 3.60 | 3.60 |
| Cocamidopropyl betaine | 5.00 | 5.00 | 5.00 |
| PEG 120 methyl glucose dioleate | 10.00 | 10.00 | 10.00 |
| Phenoxyethanol | 0.25 | 0.25 | 0.25 |
| Sodium hydroxide | 0.15 | — | — |
| Tromethamine | — | 1.50 | — |
| Polyolprepolymer 14 | 3.00 | 3.00 | 3.00 |
| Water to | 100% | 100% | 100% |

The lactic acid composition forms a clear gel having a pH 3.57 and a viscosity of 4,500 cP at 25° C.

EXAMPLE 8 - Skin Wash Composition

| Salicylic Acid | 2.00 | 2.00 | — |
|---|---|---|---|
| Lactic Acid | — | — | 1.00 |
| Decyl glucoside | 2.00 | 2.00 | 2.00 |
| Lauryl polyglucoside | 2.40 | 2.40 | 2.40 |
| Cocamidopropyl betaine | 2.80 | 2.80 | 2.80 |
| PEG 120 methyl glucose dioleate | 10.00 | 10.00 | 10.00 |
| Phenoxyethanol | 0.25 | 0.25 | 0.25 |
| Sodium hydroxide | 0.15 | — | — |
| Tromethamine | — | 1.50 | — |
| Stabylin 30 | 0.1 | 0.1 | 0.1 |
| Polyolprepolymer 14 | 3.00 | 3.00 | 3.00 |
| Water to | 100% | 100% | 100% |

The lactic acid composition forms a hazy gel having a pH 3.30 and a viscosity of 3,500 cP at 25° C.

What is claimed is:

1. An aqueous skin wash composition comprising from 0.1% to 10% w/w of an α-hydroxy acid or an acid selected from salicylic, maleic and pyruvic acid, and an amount of a detergent base in an amount not exceeding 30% w/w wherein the detergent base consists of a mixture of an amount of a non-ionic alkylpolyglucoside surfactant not exceeding 20% w/w and an amount of amphoteric surfactant not exceeding 10% w/w, and a hydroxy-terminated urethane polymer of the formula:

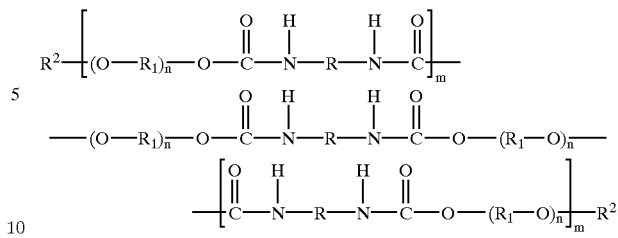

wherein:
R and $R_1$ are independently selected from an alkylene or alkenylene radical having from 1 to 20 carbon atoms, or a cycloalkylene or cycloalkenylene radical containing from 5 to 10 carbon atoms, or a mononuclear or fused ring arylene radical containing from 6 to 10 carbon atoms;

$R^2$ is selected from hydrogen, methyl or ethyl group;

m is a number in the range 0 to 6; and n is an integer in the range 8 to 51, and wherein the pH of the composition is in the range 3.0 to 4.5.

2. A composition according to claim 1 wherein the α-hydroxy acid is lactic acid.

3. A composition according to claim 2 wherein the lactic acid is present in an amount ranging from 0.1 to 5.0% w/w.

4. A composition according to claim 1 wherein the acid is salicylic acid.

5. A composition according to claim 4 wherein the salicylic acid is present in an amount ranging from 1.0 to 3.0% w/w.

6. A composition according to claim 1 wherein the hydroxy-terminated polymer is poly[oxy(methyl-1,2-ethanediyl)],α-hydro-ω-hydroxy polymer with 1,1'methylene-bis-[4,isocyanatocyclohexane].

* * * * *